United States Patent
Himsl et al.

(10) Patent No.: US 10,192,032 B2
(45) Date of Patent: Jan. 29, 2019

(54) SYSTEM AND METHOD FOR SAVING MEDICAL IMAGING DATA

(71) Applicant: General Electric Company, Schenectady, NY (US)

(72) Inventors: Johann Himsl, Riedau (AT); Stefan Denk, Ried im Innkreis (AT)

(73) Assignee: General Electric Company, Schenectady, NY (US)

( * ) Notice: Subject to any disclaimer, the term of this patent is extended or adjusted under 35 U.S.C. 154(b) by 155 days.

(21) Appl. No.: 15/347,408

(22) Filed: Nov. 9, 2016

(65) Prior Publication Data

US 2018/0129782 A1    May 10, 2018

(51) Int. Cl.
| | | |
|---|---|---|
| G06K 9/00 | (2006.01) |
| G06F 19/00 | (2018.01) |
| A61B 8/00 | (2006.01) |
| A61B 8/08 | (2006.01) |
| G06F 17/30 | (2006.01) |
| G06T 7/00 | (2017.01) |
| G16H 30/00 | (2018.01) |

(52) U.S. Cl.
CPC .......... G06F 19/321 (2013.01); A61B 8/0833 (2013.01); A61B 8/461 (2013.01); A61B 8/468 (2013.01); A61B 8/5207 (2013.01); A61B 8/5215 (2013.01); A61B 8/54 (2013.01); A61B 8/56 (2013.01); A61B 8/565 (2013.01); G06F 17/3028 (2013.01); G06F 19/00 (2013.01); G06T 7/0012 (2013.01); G16H 30/00 (2018.01); G06T 2207/10132 (2013.01); G06T 2210/41 (2013.01)

(58) Field of Classification Search
CPC ................ G06K 9/6267; G06T 7/0012; A61B 2034/105; A61B 2034/2055; A61B 34/20
USPC .................. 382/128, 131; 715/771; 709/203; 705/3; 707/E17.026; 378/4; 600/443
See application file for complete search history.

(56) References Cited

U.S. PATENT DOCUMENTS

| | | | |
|---|---|---|---|
| 6,210,327 B1 | 4/2001 | Brackett et al. | |
| 7,526,113 B2 * | 4/2009 | Jacob | G06T 7/0012 128/922 |
| 7,672,491 B2 | 3/2010 | Krishnan et al. | |
| 9,786,051 B2 * | 10/2017 | Harper | G06T 7/0014 |
| 2004/0066389 A1 | 4/2004 | Skyba et al. | |
| 2004/0204965 A1 * | 10/2004 | Gueck | G06F 17/30265 705/3 |
| 2006/0039531 A1 | 2/2006 | Neelakantan | |
| 2011/0251483 A1 | 10/2011 | Razzaque et al. | |
| 2014/0187950 A1 | 7/2014 | Torp et al. | |
| 2015/0327841 A1 * | 11/2015 | Banjanin | A61B 8/5276 600/443 |

OTHER PUBLICATIONS

International Search Report and Written Opinion for corresponding PCT application PCT/US2017/057886 dated Jan. 29, 2018; 10 pages.

* cited by examiner

Primary Examiner — Charlotte M Baker
(74) Attorney, Agent, or Firm — McCoy Russell LLP

(57) ABSTRACT

Methods and systems are provided for tagging and selectively saving medical imaging data. One example method includes acquiring medical imaging data with a medical imaging device, tagging a subset of the medical imaging data with a tag based on one or more features of the imaging data, and saving the subset of the imaging data if the tag matches a designated tag.

20 Claims, 4 Drawing Sheets

SYSTEM AND METHOD FOR SAVING MEDICAL IMAGING DATA

FIELD

Embodiments of the subject matter disclosed herein relate to medical imaging, and more particularly, to techniques for tagging and saving medical images.

BACKGROUND

An ultrasound imaging system typically includes an ultrasound probe that is applied to a patient's body and a workstation or device that is operably coupled to the probe. The probe may be controlled by an operator of the system (e.g., a sonographer) and is configured to transmit and receive ultrasound signals that are processed into an ultrasound image by the workstation or device. The workstation or device may display the ultrasound images on a display device and store the images on an internal memory or on a remote server. Ultrasound images, particularly long image sequences (e.g., cine loops), require large amounts of storage memory, including both ultrasound system memory and data archive memory. Further, such image sequences may require a large bandwidth when sent over a network to the data archive memory, potentially slowing networking speed for other applications. To reduce the amount of data sent and/or stored, a sonographer may manually choose which images of an imaging session to save and which to skip. However, manually choosing individual images and portions of image sequences to be saved may be time consuming.

BRIEF DESCRIPTION

In one embodiment, a method comprises acquiring medical imaging data with a medical imaging device, tagging a subset of the acquired medical imaging data with a first tag of a plurality of possible tags based on one or more features of the acquired medical imaging data, and storing the subset of acquired medical imaging data in a memory operatively coupled with the medical imaging device responsive to the first tag matching a designated tag.

Thus, medical imaging data, such as ultrasound imaging data, may be automatically classified and tagged by a controller of the imaging system based on the features of the imaging data. The medical imaging data may be two-dimensional or three-dimensional image data usable to generate one or more images that may be displayed on a display device, for example, and in some examples the images themselves may be tagged, while in other examples the unprocessed imaging data may additionally or alternatively be tagged. One or more designated tags may be chosen by the sonographer or the controller based on the type of exam performed, for example, and images and/or imaging data with the designated tags may be selectively saved.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
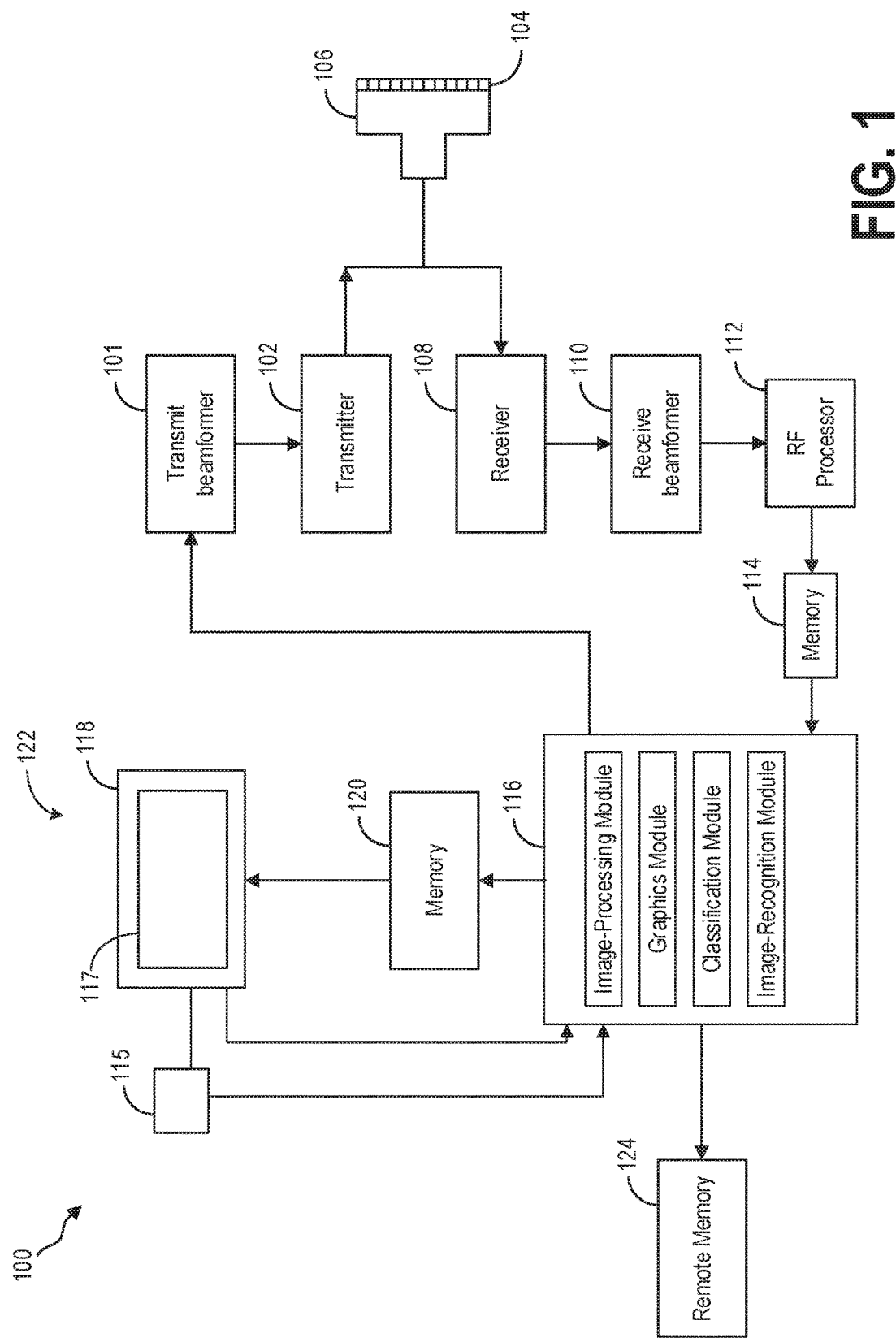
FIG. 1 shows an example ultrasonic imaging system.
Figure 2:
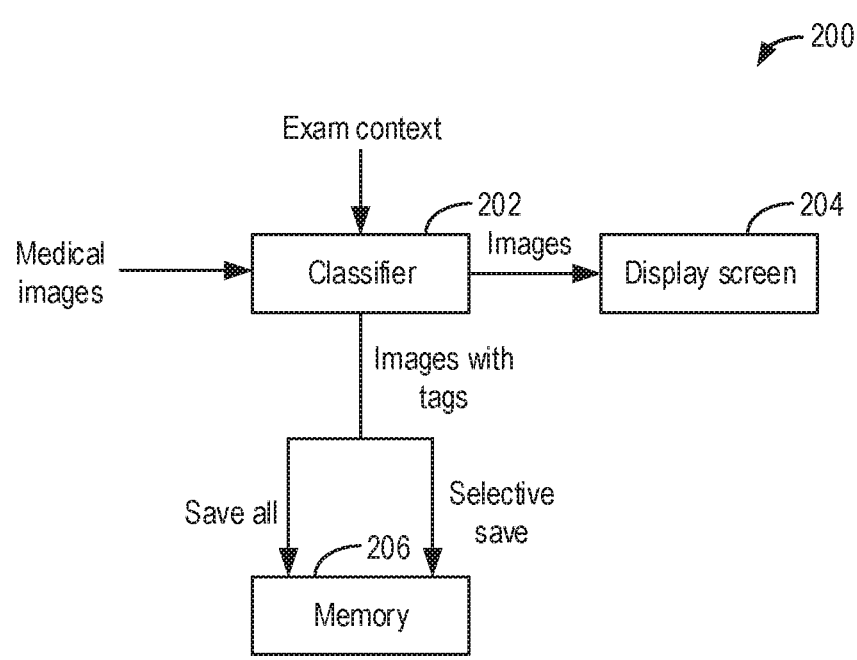
FIG. 2 shows a block diagram of a system for tagging and saving medical images.

The following description relates to various embodiments of an imaging system, such as the ultrasound imaging system shown in FIG. 1. In particular, systems and methods are provided for automatically classifying medical imaging data and tagging subsets of the imaging data (e.g., a subset of the imaging data usable to generate an image) based on features of the imaging data. As the processes described herein may be applied to pre-processed imaging data and/or to processed images, the term image is generally used throughout the disclosure to denote both pre-processed image data and processed images. Image features may include an anatomical feature (e.g., an organ), a motion of the anatomical feature, or a motion of the probe during image acquisition, for example. As shown in the diagram of FIG. 2, the system may use a classifier to apply appropriate tags to each image. Tags may be used to designate the images to be saved, for example, according to the method of FIG. 3 and the control sequence of FIG. 4. Advantages that may be realized in the practice of some embodiments of the described systems and techniques are that automating the saving process may increase exam documentation, reduce the amount of data stored, and reduce the amount of time the sonographer spends on each exam. Though the systems and methods described below for selectively saving medical images are discussed with reference to an ultrasound imaging system, it should be noted that the methods described herein may be applied to a plurality of imaging systems (e.g., MRI, PET, X-ray, or other similar systems).

FIG. 1 illustrates a block diagram of a system 100 according to one embodiment. In the illustrated embodiment, the system 100 is an imaging system and, more specifically, an ultrasound imaging system. However, it is understood that embodiments set forth herein may be implemented using other types of medical imaging modalities (e.g., MRI, CT, PET/CT, and SPECT). As shown, the system 100 includes multiple components. The components may be coupled to one another to form a single structure, may be separate but located within a common room, or may be remotely located with respect to one another. For example, one or more of the modules described herein may operate in a data server that has a distinct and remote location with respect to other components of the system 100, such as a probe and user interface. Optionally, in the case of ultrasound systems, the system 100 may be a unitary system that is capable of being moved (e.g., portably) from room to room. For example, the system 100 may include wheels or be transported on a cart.

In the illustrated embodiment, the system 100 includes a transmit beamformer 101 and transmitter 102 that drives an array of elements 104, for example, piezoelectric crystals, within a diagnostic ultrasound probe 106 (or transducer) to emit pulsed ultrasonic signals into a body or volume (not shown) of a subject. The elements 104 and the probe 106 may have a variety of geometries. The ultrasonic signals are back-scattered from structures in the body, for example, blood vessels and surrounding tissue, to produce echoes that return to the elements 104. The echoes are received by a receiver 108. The received echoes are provided to a receive beamformer 110 that performs beamforming and outputs an RF signal. The RF signal is then provided to an RF processor 112 that processes the RF signal. Alternatively, the RF processor 112 may include a complex demodulator (not shown) that demodulates the RF signal to form IQ data pairs representative of the echo signals. The RF or IQ signal data may then be provided directly to a memory 114 for storage (for example, temporary storage). In some examples, the beamformer may receive IQ data as a single channel input, and as such the beamformed signal may include IQ data.

The system 100 also includes a system controller 116 that includes a plurality of modules, which may be part of a single processing unit (e.g., processor) or distributed across multiple processing units. The system controller 116 is configured to control operation of the system 100. The system controller 116 may include an image-processing module that receives image data (e.g., ultrasound signals in the form of RF signal data or IQ data pairs) and processes image data. For example, the image-processing module may process the ultrasound signals to generate slices or frames of ultrasound information (e.g., ultrasound images) for displaying to the operator. When the system 100 is an ultrasound system, the image-processing module may be configured to perform one or more processing operations according to a plurality of selectable ultrasound modalities on the acquired ultrasound information. By way of example only, the ultrasound modalities may include color-flow, acoustic radiation force imaging (ARFI), B-mode, A-mode, M-mode, spectral Doppler, acoustic streaming, tissue Doppler module, C-scan, and elastography. The generated ultrasound images may be two-dimensional (2D) or three-dimensional (3D). When multiple two-dimensional (2D) images are obtained, the image-processing module may also be configured to stabilize or register the images.

Acquired ultrasound information may be processed in real-time during an imaging session (or scanning session) as the echo signals are received. Additionally or alternatively, the ultrasound information may be stored temporarily in the memory 114 during an imaging session and processed in less than real-time in a live or off-line operation. An image memory 120 is included for storing processed slices of acquired ultrasound information that are not scheduled to be displayed immediately. The image memory 120 may comprise a suitable data storage medium, for example, a permanent storage medium, removable storage medium, and the like. Additionally, the image memory 120 may be a non-transitory storage medium. Image memory 120 may additionally or alternatively include temporary storage, such as a first-in-first-out buffer.

The system controller 116 may be in communication (e.g., wired or wireless communication) with a remote device that includes a remote memory 124. In one example, the remote memory 124 may be part of a picture archiving and communication system (PACS) that is configured to store patient medical histories, imaging data, test results, diagnosis information, management information, and/or scheduling information, for example. The remote memory 124 may comprise a PACS server that includes computer-readable storage media suitable for storing image data for later retrieval and viewing at a PACS workstation, for example.

In operation, an ultrasound system may acquire data, for example, volumetric data sets, by various techniques (for example, 3D scanning, real-time 3D imaging, volume scanning, 2D scanning with probes having positioning sensors, freehand scanning using a voxel correlation technique, scanning using 2D or matrix array probes, and the like). Ultrasound images of the system 100 may be generated from the acquired data (at the controller 116) and displayed to the operator or user on the display device 118.

The system controller 116 is operably connected to a user interface 122 that enables an operator to control at least some of the operations of the system 100. The user interface 122 may include hardware, firmware, software, or a combination thereof that enables an individual (e.g., an operator) to directly or indirectly control operation of the system 100 and the various components thereof. As shown, the user interface 122 includes a display device 118 having a display area 117. In some embodiments, the user interface 122 may also include one or more user interface input devices 115, such as a physical keyboard, mouse, and/or touchpad. In one embodiment, a touchpad may be configured with the system controller 116 and display area 117 such that when a user moves a finger/glove/stylus across the face of the touchpad, a cursor atop the ultrasound image on the display area 117 moves in a corresponding manner. In an embodiment, the display device 118 is a touch-sensitive display (e.g., touchscreen) that can detect a presence of a touch from the operator on the display area 117 and can also identify a location of the touch in the display area 117. The touch may be applied by, for example, at least one of an individual's hand, glove, stylus, or the like. As such, the touch-sensitive display may also be characterized as an input device that is configured to receive inputs from the operator. The display device 118 also communicates information from the controller 116 to the operator by displaying the information to the operator. The display device 118 and/or the user interface 122 may also communicate audibly. The display device 118 is configured to present information to the operator during the imaging session. The information presented may include ultrasound images, graphical elements, user-selectable elements, and other information (e.g., administrative information, personal information of the patient, and the like).

In addition to the image-processing module, the system controller 116 may also include a graphics module, a classification module, and an image recognition module. The image-processing module, the graphics module, the classification module, and the image recognition module may coordinate with one another to present information to the operator during and/or after the imaging session. For example, the image-processing module may be configured to display an acquired image on the display device 118, and the graphics module may be configured to display designated graphics along with the ultrasound image, such as graphical outlines that represent lumens or vessel walls in the acquired image. The image-processing and/or graphics modules within the system controller 116 may also be configured to generate a 3D rendering or image (not shown) of an imaged structure.

The system controller 116 may also house an image-recognition module, which accesses stored images/videos (i.e., an image library) from either or both of the memory 114 and the memory 120 and analyzes the images/videos in order to identify one or more features within each image. For example, knowing the parameters under which a protocol is being carried out (ultrasound type, scan plane, tissue being imaged, etc.), the image recognition module may compare a live image on the display area 117 to one stored in memory 120 in order to classify the image with appropriate tags based on the anatomical feature being imaged, as described later on with reference to FIG. 3. As used herein, "tag" refers to a descriptive or identifying label that may be associated with an image in order to classify the image for subsequent processing, such as subsequent selective save (as will be described in more detail below). The tag may include computer-readable information included within the image data (e.g., as metadata) of the image or as a separate file from the image that includes additional information usable by a computing device to associate the tag with the image.

Additionally or alternatively, the image recognition module may use a model or algorithm stored within a memory of the controller, such as a shape detection algorithm, to recognize the anatomical feature and apply a corresponding tag. For example, the image recognition module may house both an image library and separate instructions for analyzing the displayed image/video apart from an image library, and both of these approaches may be used for anatomical feature recognition and tagging. Further, the system controller may house instructions for analyzing acquired imaging data (e.g., ultrasound images/videos acquired with the probe), such as via the image-recognition module, and tagging the acquired imaging data (via the classification module, for example) based on recognized features of the image, periodic motion within the imaging data, the motion of the ultrasound probe, etc., as described further with reference to FIG. 3.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

The screen of the display area 117 of the display device 118 is made up of a series of pixels that display the data acquired with the probe 106. The acquired data include one or more imaging parameters calculated for each pixel or group of pixels (for example, a group of pixels assigned the same parameter value) of the display, where the one or more calculated image parameters includes one or more of an intensity, velocity, color flow velocity, texture, graininess, contractility, deformation, and rate of deformation value. The series of pixels then make up the displayed image generated from the acquired ultrasound data. As mentioned above, the data acquired with the probe 106 and processed by the controller 116 may be 2D or 3D data. For example, traditionally, B-mode images, otherwise known as 2D images, may be generated from A-mode information. In A-mode, where A stands for amplitude, information of the reflected signal in a single ultrasound beam is continually displayed as distance from the probe and intensity, which are shown by position and amplitude in a line on an oscilloscope. A-mode information from many beams typically forms a sector in a plane of the body, which is then shown as pixel intensity on a monitor in what is known as B-mode, where B stands for brightness. B-mode may be used for anatomic localization, assessment, and orientation in the body and as a background display of other information (e.g, Doppler signals), and may also include 3D imaging data. B-mode information, which may include 2D images, volume data, and/or sequences of data, may be used to perform feature recognition and subsequently tag the image with one or more tags corresponding to the recognized feature.

A 3D medical imaging dataset acquired with the probe 106 includes a volume dataset including a plurality of voxels. Each voxel, or volume-element, is assigned a value or intensity. Additionally, each voxel may be assigned an opacity as well. The value or intensity may be mapped to a color according to some embodiments. As one example, a volume-rendered image may be generated from the 3D dataset using a ray casting technique. For example, the controller 116 may cast a plurality of parallel rays from a view plane of the display 118 (which comprises the series of pixels) through the 3D medical imaging dataset. It should be appreciated that multiple rays may be cast in order to assign values to all of the pixels within the view plane. The controller 116 may use a "front-to-back" or a "back-to-front" technique for volume composition in order to assign a value to each pixel in the view plane that is intersected by the ray. For example, starting at the front—that is, the direction from which the image is viewed—the intensities of all the voxels along the corresponding ray may be summed. An opacity value, which corresponds to light attenuation, is assigned to each voxel. The intensity is multiplied by the opacity of the voxels along the ray to generate an opacity-weighted value. These opacity-weighted values are then accumulated in a front-to-back or in a back-to-front direction along each of the rays. The process of accumulating values is repeated for each of the pixels in the view plane in order to generate a volume-rendered image. In this way, each pixel used to form the image displayed on the display 118 may have an intensity, or brightness, value associated with it.

As described in detail with reference to FIG. 1, a controller of an ultrasound system processes ultrasound data to generate an ultrasound image. The ultrasound image may be displayed to an operator on a display screen (such as touch-sensitive display screen 118 of FIG. 1) and/or stored in memory (e.g., memory 120 and/or remote memory 124 of FIG. 1) for later review by a clinician. Traditionally, sonographers manually choose which images to skip and which images to save, which adds time to the ultrasound exam. Furthermore, long scan sequences require large amounts of memory for storage. An imaging workflow that automatically saves images of interest based on the content of the image matching a desired content and discards other images may reduce exam time and reduce storage requirements, as described in more detail below.

Turning now to FIG. 2, a block diagram of a system 200 for classifying and saving images acquired by a medical imaging system (e.g., system 100 of FIG. 1) is illustrated. System 200 includes a classifier 202, display screen 204, and memory 206. Display 118 of FIG. 1 is a non-limiting example of display screen 204 and memory 120 and/or remote memory 124 may be non-limiting examples of memory 206. Classifier 202 may be a module in the system controller (such as the classification module of the controller 116 of FIG. 1) that includes algorithms to automatically classify one or more images acquired by the medical imaging system based on identified features of the image, such as anatomical features (as determined by an image-recognition module, such as the image-recognition module of the controller 116 of FIG. 1), exam type, probe motion, progress through an imaging protocol, etc.

Accordingly, medical images (which may include imaging data usable to generate images and/or processed images, and may further include two-dimensional imaging data and/or three-dimensional imaging data) may be input into the classifier along with exam context (such as the exam type, the probe used, scan plane, etc.) in some examples. The exam context may be provided via user input or determined automatically by the system controller. As one example, a system operator may manually input the exam context, such as by selecting exam operating parameters from a list of possible operating parameters or by selecting a pre-programmed imaging protocol. As another example, the imaging system may automatically detect the type of probe used, which may be associated with a particular exam type (e.g., a transvaginal ultrasound probe for a pelvic exam) or imaging mode (e.g., B-mode). Based on the received medical images and exam context, classifier 202 may generate one or more tags corresponding to the identified features of the images and apply the tags to individual images and/or images in a cine, as described in detail below with reference to FIG. 3. Images may be displayed on the display screen 204 simultaneously with the tagging of the images, subsequent to the tagging of the images, or prior to the tagging of the images.

Images with tags generated by classifier 202 may be saved to the memory 206. As one example, such as when the user of the system has not designated a selective save mode, all of the images are saved to memory 206 regardless of the tag(s) associated with each image. However, saving all of the images requires a large amount of storage memory. Additionally, such a relatively large amount of saved images may pose a time burden on a clinician reviewing the images, which may unsuitably delay a diagnosis, for example. Therefore, as another example, only images with the desired tag(s) are saved, such as when the user designates a selective save mode, as described in detail with reference to FIG. 3. As still another example, images with the desired tag(s) may be saved to a different memory than images that do not contain the desired tag(s). For example, images with the desired tag(s) may be saved to a PACS server memory (e.g., remote memory 124 of FIG. 1), and images that do not contain the desired tag(s) may be saved to an internal memory of the medical imaging system (for example, memory 120 of FIG. 1). In a still further example, all of the images, regardless of tags, may be saved to a first, temporary memory, such as a buffer or other temporary storage on the ultrasound system workstation, while only the tagged images matching a desired tag may be saved to a second, remote memory, such as a PACS. The desired tag(s) may be manually selected by the operator (e.g., input via a user interface), automatically selected by the system controller (for example, based on the type of exam performed or the imaging protocol), or through a combination of manual selection and automatic selection.

As described above, the medical imaging device (e.g., ultrasound imaging device) may acquire medical imaging data, which may include two-dimensional and/or three-dimensional data, that may be processed into one or more images for subsequent displaying and/or tagging. The processed images may be tagged in the manner described. Additionally or alternatively, the (pre-processed) imaging data may be tagged. For example, volumetric 3D imaging data may be processed to generate a plurality of images (e.g., various 2D images taken at slices of the volumetric dataset), and it may be desirable to save the entire volumetric dataset to allow a clinician or other operator to view various slices and/or cine loops taken from the volumetric dataset at a later time. Thus, the classifier may classify a volumetric dataset or other pre-image processing image data in order to apply one or more tags to the imaging data and selectively save different imaging datasets (e.g., taken at different points in time during a scanning session).

In one example, a medical imaging dataset may include a volumetric 3D imaging dataset that includes a feature of interest, such as a heart. The classifier may apply a recognized feature tag (e.g., a heart tag) to the volumetric dataset, along with other applicable tags, such as a 3D data tag. Then, during the course of imaging, an operator may request to view various slices of the volumetric dataset as images on a display device, and the classifier may tag each processed image with applicable tags, including the heart tag as well as more specific tags, such as subanatomical feature tags (e.g., interventricular septum). During a selective save process, the volumetric dataset may be saved as well as the images that include the interventricular septum (e.g., the controller may be configured to save imaging data that is tagged with both 3D data and heart, and also save imaging data that is tagged with both heart and interventricular septum). In this way, the volumetric dataset(s) relevant to the feature of interest (e.g., the heart) may be saved as well as specific images viewed during imaging (those images that include the interventricular septum).

Figure 3:
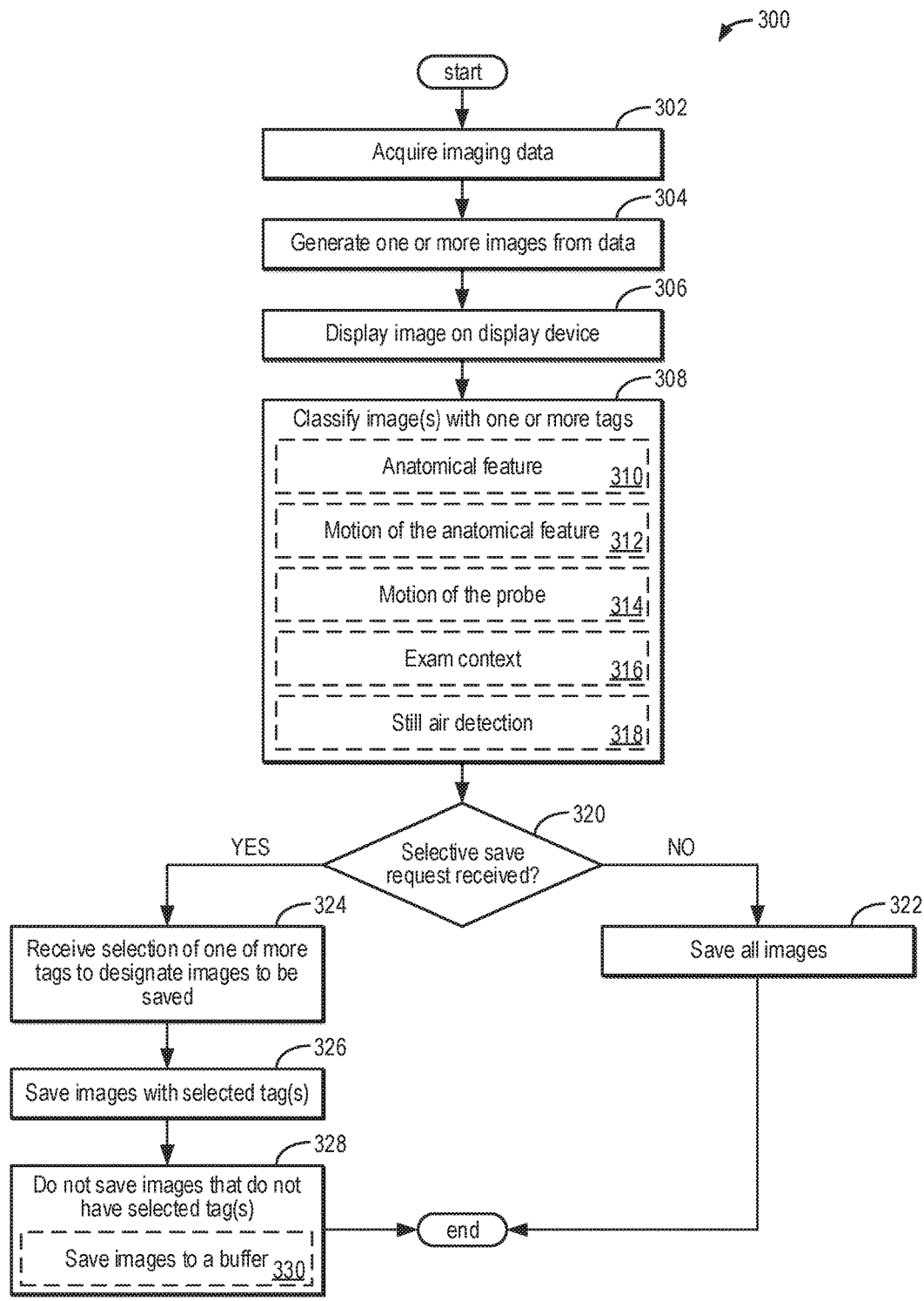
FIG. 3 is a flow chart illustrating a method for classifying ultrasound images with tags and selectively saving images with certain tags.

Turning to FIG. 3, a flow chart of a method 300 for classifying images with tags and selectively saving images with designated tags is shown. The method 300 may be performed with an imaging system, such as the ultrasound imaging system 100 shown in FIG. 1. More specifically, method 300 may be executed by a controller of the ultrasound imaging system (such as controller 116 shown in FIG. 1) according to instructions stored on a non-transitory memory of the system (e.g., memory 120 shown in FIG. 1) in combination with the various signals received at the controller from the system components and actuation signals sent from the system controller to the display device. However, according to other embodiments, the method 300 may also be performed with other ultrasound imaging systems or with different medical imaging devices (e.g., MRI, PET, X-ray, or other similar systems).

Method 300 begins at 302, where the ultrasound imaging system acquires a medical imaging dataset obtained with an ultrasound probe (such as ultrasound probe 106 shown in FIG. 1). The acquired medical imaging dataset may include two-dimensional data and/or three-dimensional data (e.g., a volume dataset). In an example, imaging data may be acquired according to an ultrasound image acquisition protocol. For example, the image acquisition protocol may include a plurality of anatomical structures to be imaged during an imaging session. The image acquisition protocol may include instructions displayed on the user interface, for example, to guide an operator through the acquisition of designated images. However, in other examples, the image acquisition protocol may include instructions for the ultrasound system to automatically acquire some or all of the images or perform other functions (e.g., the image acquisition protocol may include instructions to automatically move the ultrasound probe, initiate and/or terminate a scanning process, and/or adjust imaging parameters of the ultrasound probe parameters, such as ultrasound signal transmission parameters, ultrasound signal receive parameters, ultrasound signal processing parameters, or ultrasound signal display parameters).

At 304, the method includes generating one or more ultrasound images from the acquired ultrasound data. For example, the signal data acquired during the method at 302 is then processed and analyzed by the system controller (e.g., such as controller 116 shown in FIG. 1) in order to produce an ultrasound image. The system controller may include an image-processing module that receives the signal data (e.g., image data) acquired at 302 and processes the received image data. For example, the image-processing module may process the ultrasound signals to generate slices or frames of ultrasound information (e.g., ultrasound images) for displaying to the operator. In one example, generating the image may include determining an intensity value for each pixel of a display screen (e.g., touch-sensitive display 118 shown in FIG. 1) based on the received image data (e.g., 2D or 3D ultrasound data). As such, the ultrasound images may be two-dimensional (2D) or three-dimensional (3D) depending on the mode of ultrasound being used (e.g., color-flow, acoustic radiation force imaging, B-mode, A-mode, M-mode, spectral Doppler, acoustic streaming, tissue Doppler module, C-scan, and elastography).

At 306, the method includes displaying the generated ultrasound image(s) on a display (e.g., touch-sensitive display 118 shown in FIG. 1). For example, the method at 306 may include the real-time display of the generated image(s) while data is being acquired with the ultrasound probe.

At 308, the method includes classifying the image(s) with one or more tags. For example, the system controller may include an image classification module (such as classifier 202 of FIG. 2) that automatically applies relevant tags to individual images during an imaging session based on the content of the image and the context in which the image was acquired. In one example, a tag may specify an anatomical feature, as indicated at 310. The anatomical feature may be an organ (e.g., a heart) or a region of an organ (e.g., an aorta of a heart), for example. Such an analysis may be useful in obstetrics, for example, where features of the fetus (e.g., head, heart) may be tagged. In one embodiment, the classifier module may use image recognition algorithms to identify the anatomical feature. For example, the classifier may utilize a shape detection algorithm specifically tuned to identify the shape of the desired anatomical feature based on training data.

The image recognition algorithms employed may be different for different types of imaging data. During 2D B-mode imaging, an image may only include a slice of an organ, and thus an image recognition algorithm that is configured to recognize the organ itself may be used. In cardiology or fetal cardiology, a sequence of images may be used to detect periodic motion typical of the heart or fetal heart, and as such a different or modified image recognition algorithm may be used. Applications suited for volume data acquisitions may utilize specialized algorithm architectures. Conventional approaches such as convolutional neural networks may be adapted to the 3D data sets, and the processing of the extra dimension compared to 2D images significantly enlarges the data sets. The reduction of the 3D datasets to 2D images via rendering or extracting special planes is also possible, but would not make use of the full information contained in volume data sets. Instead, organs may be detected directly in the 3D volume by locating predefined shapes. As such a localization utilizes the determination of six parameters (three angles of rotation, three for position), the algorithms may be based on simplified shapes to reduce computational efforts. When a shape associated with a given organ is successfully located in the volume, the tag corresponding to this organ is then added to the volume.

As indicated at 312, another example of a tag may include the motion of the anatomical feature (e.g., a beating heart). For example, the controller may compare changes in pixel (or voxel) intensity in a series of images, and in the absence of ultrasound probe movement, as elaborated below, a change in pixel intensity at a given coordinate may be assumed to denote motion of the anatomical feature.

In another example, an image may be tagged based on the motion of the ultrasound probe, as indicated at 314. For example, the controller may detect a predetermined motion pattern based on a motion sensing system mounted on the ultrasound probe (such as probe 106 of FIG. 1). The motion sensing system may include one or more of an accelerometer, a gyro sensor, and a magnetic sensor, for example. Position data from the motion sensing system may be used to detect different types of motion (e.g., translation, lifting, rolling, and twisting). Controller 116 may convert position data from the motion sensing system into linear and angular velocity signals. Next, the controller may convert the linear and angular velocity signals into 2D or 3D movements, which may be used as inputs for performing gesture recognition, such as for detecting a predetermined motion pattern. As such, the classifier may tag images that were acquired during a predetermined probe motion pattern. In other examples, such as when a motion sensing system is not available, the motion of the probe may be detected by an analysis of the image sequences. Probe motion may indicate that the operator of the ultrasound probe has moved the probe over a feature of interest (e.g., an organ) to get a desired view of the feature, and as such the entire sequence of images while moving the probe may be of interest to the operator and hence may be tagged for subsequent selective save. The probe motion tagging may include probe motion velocity, probe motion direction, and the like.

Furthermore, as indicated at 316, exam context may provide additional image tags, including the parameters in which the protocol is being performed (ultrasound type, scan plane, tissue being imaged, etc.), as well as filter the possible tags for the imaging session from an exhaustive pool of tags that may be applied to an image. For example, the exam context may include the type of exam being performed (such as a fetal anatomy scan, echocardiogram, abdominal ultrasound, etc.). As such, the controller will be given a context for the types of features to identify and may therefore limit the possible tags to apply to the resulting images based on the context. For example, if an abdominal ultrasound exam is performed, the controller may be programmed to identify organs such as the liver, gallbladder, and pancreas in the resulting ultrasound images. Similarly, as an abdominal ultrasound exam does not involve imaging the heart, the controller may not attempt to recognize and tag the heart in the resulting ultrasound images. Additionally, the exam context may include different steps within a multi-step image acquisition protocol. As described above, the ultrasound image acquisition protocol may include a predefined list of anatomical structures and features to be imaged and measured during an exam. The system may know that a certain step in the protocol is being performed (and thereby know which feature is being imaged) based on user input or based on an automatic progression of the protocol. For example, the imaging acquisition protocol may prompt the sonographer to image the liver during an abdominal ultrasound exam, and the controller may perform feature recognition on all of the images obtained during that portion of the protocol. By utilizing the exam context to selectively perform feature recognition and subsequent image tagging (e.g., only performing feature recognition to determine if an image includes a liver rather than identifying all features within the image), the processing time and/or power required for performing the feature recognition and tagging may be reduced, thus allowing the system controller to operate more efficiently.

Still air detection may be included as an image tag, as indicated at 318. Still air detection may signal that the patient is no longer being scanned (that is, the probe has been lifted). The above examples are explanatory in purpose and are not meant to limit the types of tags that may be applied to an image using example method 300, as other types of tags are within the scope of the disclosure.

At 320, the method includes determining if a selective save request is received. A selective save request may be input by the operator or may be included as part of a programmed image acquisition protocol. If a selective save request is not received, method 300 progresses to 322 and includes saving all of the images from the imaging session. For example, the images may be saved to a PACS server, such as remote memory 124 of FIG. 1, or to a permanent memory of the ultrasound system, such as memory 120 of FIG. 1. Following 322, method 300 ends.

Returning to 320, if a selective save request is received, the method proceeds to 324 and includes receiving the selection of one or more tags to designate the images to be saved. For example, the operator may input tag selections based on the type of exam performed. In another example, the controller may automatically select relevant tags based on the image acquisition protocol performed.

At 326, the method includes saving the images that have been tagged with tag(s) that match the selected tag(s) designated at 326. The images with the selected tag(s) may be saved to an internal memory of the ultrasound system or to a remote memory (for example, a PACS server). In one example, an image will be saved if it is tagged with at least one of the selected tags. In another example, an image may be saved only if the image is tagged with all of the selected tags.

At 328, method 300 includes not saving the images that do not have the selected tags(s) (as selected at 324). For example, images without the selected tag(s) may be deleted. As indicated at 330, the images that do not have the selected tag(s) may optionally be saved to a buffer memory or other temporary memory. This may include temporarily storing the images without the selected tag(s) in the memory of the ultrasound system (e.g., memory 114 of FIG. 1) until the end of the imaging session, for example. As another example, the images may be temporarily stored for a fixed duration (e.g., one day) to allow a sonographer or clinician to review additional images from the imaging session, if necessary.

Further, in one example, a selective skip may be performed based on the tag(s) associated with the image. As explained above, an image may be tagged with a still air tag when still air is detected. Because any images captured during probe still air would not include imaged tissue or other features, the images that are tagged with a still air tag may be skipped (e.g., deleted) rather than saved.

In this way, the method 300 streamlines a medical imaging workflow by automatically tagging images and selectively saving images with the designated tag(s) responsive to user input or to a predetermined protocol. By automating the image saving process, scan documentation may be increased, with less variation between sonographers. Further, the method 300 also reduces storage memory requirements for both the ultrasound system and long-term, archival storage by only saving images of interest.

While method 300 was described above as including image classification that occurs continuously during imaging while the saving of tagged images is performed selectively, in some examples the tagging could also be performed selectively. For example, if the selective save request is not received (e.g., the operator does not enter an input to perform selective save), the controller may not tag the images and may instead automatically save all images or allow the operator to select which images to save. In this way, the processing power used during the image tagging may be conserved by only tagging images when the selective save process is to be performed.

Further, the method described above included automatically tagging the images e.g., without explicit operator input at the time of tagging. However, in some examples the operator may choose to tag certain images to be saved or deleted, and as such a manual tag process may be performed. For example, the operator may enter a user input (e.g., toggle a manual save button on the ultrasound probe) during scanning or when viewing displayed images to manually tag one or more images for saving or deleting. In this way, the operator may ensure high priority images are saved regardless of the selective save performed by the system controller.

Figure 4:
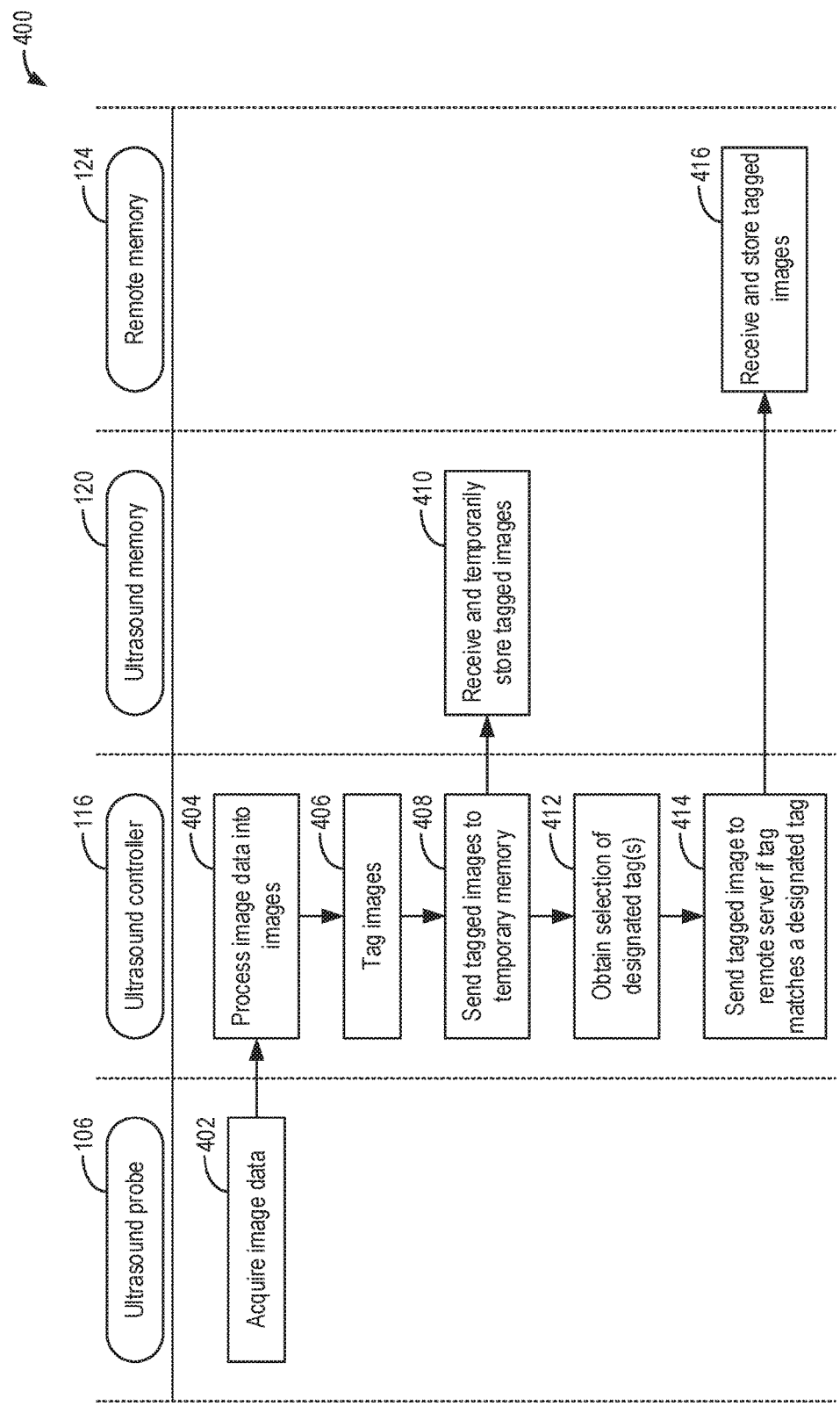
FIG. 4 is a diagram illustrating an example control sequence for selectively saving tagged images.

FIG. 4 illustrates a non-limiting example of a timing diagram 400 that illustrates example actions of components of the system 100 that may occur during the execution of the method 300. Beginning at 402, the ultrasound probe 106 acquires image data. At 404, the ultrasound controller 116 processes the image data into one or more images. At 406, the ultrasound controller 116 tags the images and, at 408, sends the tagged images to a temporary memory. At 410, the ultrasound memory 120 receives and temporarily stores the tagged images. At 412, the ultrasound controller 116 obtains the selection of one or more designated tags. At 414, the ultrasound controller 116 sends each tagged image to a remote server if a respective image tag matches a designated tag. The remote memory 124 receives and stores the tagged images at 416. In an alternative example, images with the designated tags are sent from the ultrasound memory 120 to the remote memory 124 for permanent storage.

In the example illustrated in FIG. 4, images with the designated tag(s) are selectively saved to the remote memory 124 for permanent storage. In an alternative example, the ultrasound memory 120 is a permanent memory, and images with tags matching the designated tag(s) may be saved to the ultrasound memory 120 for permanent storage. In still another example, rather than selectively saving images with the designated tag(s) to the ultrasound memory 120 for permanent storage, images lacking the designated tag(s) are selectively deleted from the ultrasound memory. Further, rather than only storing the tagged images in temporary memory, all images may be saved in the temporary memory, and the images may be tagged while stored in the temporary memory.

Thus, the systems and methods described herein provide for selective saving of one or more images obtained during an imaging session. The images obtained during the imaging session may be tagged based on features of the image, such as recognized anatomical features (e.g., organs, vasculature, and bones present in the images), motion of the anatomical features, imaging parameters when the image was acquired (e.g., type of medical imaging performed, motion of the imaging device), anatomical features of interest specified by an operator and/or by an automated image acquisition protocol, and/or other features. One or more tags may be selected (by an operator or automatically by the system) as designated tags for saving, and any images that include tags that match the designated tags may be saved in permanent memory.

In one example, a segment of an image acquisition protocol may be initiated that specifies a certain anatomical feature be imaged, such as the heart. During this segment of the image acquisition protocol, the imaging system may be controlled (automatically or by the operator) to obtain images including the heart. However, some images may be captured that do not include the heart, such as when the heart is initially being located. All images during the segment may be tagged with the anatomical features recognized in the images, and the image acquisition protocol may indicate to the system to save all images tagged with a heart tag. Accordingly, the images acquired during the segment that have been tagged with the heart image may be saved while the images acquired during the segment that have not been tagged with the heart tag may not be saved (e.g., the images acquired at the beginning of the segment before the heart is located).

During a single imaging session, the tags selected as the designated tags for saving images may change over the course of the imaging session. For example, following the segment described above, a second segment of the image acquisition protocol may be initiated that specifies another anatomical feature to be imaged, such as the liver. During the second segment of the image acquisition protocol, the images tagged with a liver tag may be saved while the images not tagged with a liver tag may not be saved, even if those images are tagged with a heart tag. Accordingly, the selective save may be performed in a temporally specific manner, such that the types of images selected to be saved may change over time. However, some tags may be designated to be saved (or deleted) regardless of the progress through an imaging protocol, such as deleting any images tagged with a still air tag regardless of the timing of when those images were acquired.

The technical effect of selectively saving images based on one or more user- or system-designated tags is to reduce the amount of medical image data storage and increase operator efficiency.

In one embodiment, a method comprises acquiring medical imaging data with a medical imaging device; tagging a subset of the acquired medical imaging data with a first tag of a plurality of possible tags based on one or more features of the acquired medical imaging data; and storing the subset of the acquired medical imaging data in a memory operatively coupled with the medical imaging device responsive to the first tag matching a designated tag. The subset of the acquired medical imaging data may be saved in memory as a processed image or as unprocessed imaging data usable to generate an image.

In an example, the method further comprises receiving a user input selecting the designated tag. In another example, the method further comprises selecting the designated tag responsive to a position within a predetermined imaging protocol. The method may further comprise selecting the designated tag responsive to an imaging mode used to acquire the medical imaging data. The acquired medical imaging data may include one or more of two-dimensional data and three-dimensional data. The subset of acquired medical imaging data may be usable to generate an image, and tagging the subset of acquired medical imaging data may include tagging the image with the first tag In examples, tagging the subset of the acquired medical imaging data comprises performing feature recognition on the subset of the acquired medical imaging data and, responsive to identifying a recognized feature of the subset of the acquired medical imaging data, tagging the subset of the acquired medical imaging data with the first tag. In an example, the recognized feature is an anatomical feature of tissue being imaged, and the first tag corresponds to the anatomical feature. In an example, the subset of the acquired medical imaging data may be a first subset of the acquired medical imaging data, the method may further comprise performing feature recognition on each subset of the acquired medical imaging data, the feature may be periodic motion detected from the subsets of the acquired medical imaging data, and the first tag may correspond to the periodic motion.

In an example, acquiring medical imaging data with the medical imaging device comprises acquiring medical imaging data with an ultrasound probe. The method may further comprise obtaining motion data of the ultrasound probe during the acquiring of the medical imaging data, and tagging the subset of the acquired medical imaging data may comprise tagging the subset of the acquired medical imaging data with the first tag based on the motion data. The method may further comprise selecting the designated tag responsive to a type of ultrasound probe used to acquire the medical imaging data.

In examples, the designated tag comprises a first designated tag, and the method further includes tagging the acquired medical imaging data with a second tag, different than the first tag, and storing the image in the memory responsive to the second tag matching a second designated tag. In examples, the method further includes tagging the subset of the acquired medical imaging data with a second tag responsive to a user input. In some examples, the method may further comprise, when the first tag does not match the designated tag, not storing the image in the memory. For example, when the first tag does not match the designated tag, the image may be deleted from memory, or the image may be maintained in a temporary storage during a duration of a scanning session and not moved to permanent memory.

An embodiment of an ultrasound imaging system includes an ultrasound probe; a display; and a controller. The controller is configured to: acquire ultrasound data via the ultrasound probe; generate an image from the acquired data; display the image via the display; automatically classify the image with one or more selective save tags based on one or more features of the acquired data; and responsive to a tag of the one or more selective save tags matching a designated tag, store the image in a memory operatively coupled with the medical imaging device. In an example, the memory comprises a remote server communicatively coupled to the controller.

The controller may be configured to obtain an exam context defining one or more parameters of an ultrasound scanning session during which the ultrasound data is acquired. To automatically classify the image with one or more selective save tags based on one or more features of the acquired data, the controller may be configured to automatically classify the image with one or more selective save tags based on the exam context. The one or more parameters of the exam context may include one or more of an ultrasound probe type, scanning mode, and feature of interest to be scanned.

In one example, to automatically classify the image with one or more selective save tags based on one or more features of the acquired data, the controller may be configured to automatically classify the image with one or more selective save tags based on one or more of a feature identified in the image, detected motion of an identified feature of the image, and detected motion of the probe. In an example, the image is a first image, and the controller is further configured to automatically classify a second image with a selective skip tag responsive to detection of still air, and responsive to classifying the second image with the selective skip tag, the controller is configured to not save the second image in the memory.

An embodiment relates to ultrasound imaging system that includes an ultrasound probe and a processor configured to: obtain a feature of interest to be scanned by the ultrasound probe from a scanning checklist; generate a plurality of images from ultrasound data acquired via the ultrasound probe; send the plurality of images to a buffer memory; automatically tag each image of the plurality of images that includes the feature of interest; and send each tagged image to a permanent memory. In an example, the processor and buffer memory are housed in a common device, and the permanent memory is housed in a remote device.

In an example, the feature of interest is an anatomical organ, and to automatically tag each image that includes the anatomical organ, the processor may be configured to perform a feature recognition routine on each image of the plurality of images to identify each image that includes the anatomical organ, and automatically tag each identified image. In an example, the processor may be configured to adjust the feature recognition routine based on one or more of the feature of interest and imaging mode used to acquire the ultrasound data.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   acquiring medical imaging data with a medical imaging device;
   tagging a subset of the acquired medical imaging data with a first tag of a plurality of possible tags based on one or more features of the acquired medical imaging data, the one or more features including an anatomical feature;
   storing the subset of the acquired medical imaging data in a memory operatively coupled with the medical imaging device responsive to the first tag matching a designated tag; and
   not storing a remainder of the acquired medical imaging data, the remainder not tagged with the first tag, to reduce an amount of data stored in the memory.

2. The method of claim 1, further comprising one or more of receiving a user input selecting the designated tag, selecting the designated tag responsive to a position within a predetermined imaging protocol, and selecting the designated tag responsive to an imaging mode used to acquire the medical imaging data.

3. The method of claim 1, wherein the acquired medical imaging data comprises one or more of two-dimensional data or three-dimensional data.

4. The method of claim 1, wherein the subset of acquired medical imaging data is usable to generate an image, and wherein tagging the subset of acquired medical imaging data comprises tagging the image with the first tag.

5. The method of claim 1, wherein tagging the subset of the acquired medical imaging data comprises performing feature recognition on the subset of the acquired medical imaging data and, responsive to identifying a recognized feature of the subset of the acquired medical imaging data, tagging the subset of the acquired medical imaging data with the first tag.

6. The method of claim 5, wherein the recognized feature is an anatomical feature of tissue being imaged, and wherein the first tag corresponds to the anatomical feature.

7. The method of claim 5, wherein the subset of the acquired medical imaging data is a first subset of the acquired medical imaging data, wherein the method further comprises performing feature recognition on each subset of the acquired medical imaging data, wherein the feature is periodic motion detected across each subset of the acquired medical imaging data, and wherein the first tag corresponds to the periodic motion.

8. The method of claim 1, wherein the designated tag comprises a first designated tag, and further comprising tagging the acquired medical imaging data with a second tag, different than the first tag, and storing the image in the memory responsive to the second tag matching a second designated tag.

9. The method of claim 1, wherein acquiring medical imaging data with the medical imaging device comprises acquiring medical imaging data with an ultrasound probe, and further comprising obtaining motion data of the ultrasound probe during the acquiring of the medical imaging data, and wherein tagging the subset of the acquired medical imaging data comprises tagging the subset of the acquired medical imaging data with the first tag based on the motion data.

10. The method of claim 1, further comprising tagging the subset of the acquired medical imaging data with a second tag responsive to a user input.

11. The method of claim 1, further comprising, when the first tag does not match the designated tag, not storing the subset of the acquired medical imaging data in the memory.

12. An ultrasound imaging system, comprising:
an ultrasound probe;
a display; and
a controller configured to:
acquire ultrasound data via the ultrasound probe;
generate an image from the acquired data;
display the image via the display;
automatically classify the image with one or more selective save tags based on one or more features of the acquired data, the one or more features including an anatomical feature;
responsive to a tag of the one or more selective save tags matching a designated tag, store the image in a memory operatively coupled with a medical imaging device; and
responsive to none of the one or more selective save tags matching the designated tag, deleting the image without storing the image in the memory to reduce an amount of image data storage.

13. The system of claim 12, wherein the memory comprises a remote server communicatively coupled to the controller.

14. The system of claim 12, wherein the controller is configured to obtain an exam context defining one or more parameters of an ultrasound scanning session during which the ultrasound data is acquired, and wherein to automatically classify the image with one or more selective save tags based on the one or more features of the acquired data, the controller is configured to automatically classify the image with one or more selective save tags based on the exam context, the one or more parameters comprising one or more of an ultrasound probe type, a scanning mode, and a feature of interest to be scanned.

15. The system of claim 12, wherein to automatically classify the image with one or more selective save tags based on the one or more features of the acquired data, the controller is configured to automatically classify the image with one or more selective save tags based on one or more of a feature identified in the image, detected motion of an identified feature of the image, and detected motion of the probe.

16. The system of claim 12, wherein the image is a first image, and wherein the controller is further configured to automatically classify a second image with a selective skip tag responsive to detection of still air, and, responsive to classifying the second image with the selective skip tag, the controller is configured to not save the second image in the memory.

17. An ultrasound imaging system, comprising:
an ultrasound probe; and
a processor configured to:
obtain a feature of interest to be scanned by the ultrasound probe from a scanning checklist;
generate a plurality of images from ultrasound data acquired via the ultrasound probe;
send the plurality of images to a buffer memory;
perform a feature recognition routine on each image of the plurality of images to identify each image that includes the feature of interest, the feature recognition routine including a shape detection algorithm;
automatically tag each identified image of the plurality of images that includes the feature of interest;
send each tagged image to a permanent memory; and
delete the plurality of images from the buffer memory after sending each tagged image to the permanent memory to reduce an amount of image data storage.

18. The ultrasound imaging system of claim 17, wherein the processor and the buffer memory are housed in a common device and the permanent memory is housed in a remote device.

19. The ultrasound imaging system of claim 17, wherein the feature of interest is an anatomical organ, and wherein to automatically tag each image that includes the anatomical organ, the processor is configured to perform the feature recognition routine on each image of the plurality of images to identify each image that includes the anatomical organ, and automatically tag each identified image.

20. The ultrasound imaging system of claim 17, wherein the processor is configured to adjust the feature recognition routine based on one or more of the feature of interest and an imaging mode used to acquire the ultrasound data.

* * * * *